(12) United States Patent  (10) Patent No.: US 8,690,963 B2
Puchhammer  (45) Date of Patent: *Apr. 8, 2014

(54) ARTICULATED HAND PROSTHESIS (75) Inventor: Gregor Puchhammer, Wien (AT)

(73) Assignee: Otto Bock Healthcare GmbH, Duderstadt (DE)

( * ) Notice: Subject to any disclaimer, the term of this patent is extended or adjusted under 35 U.S.C. 154(b) by 518 days.

This patent is subject to a terminal disclaimer.

(21) Appl. No.: 12/158,579

(22) PCT Filed: Dec. 21, 2006

(86) PCT No.: PCT/DE2006/002310
§ 371 (c)(1),
(2), (4) Date: Jun. 20, 2008

(87) PCT Pub. No.: WO2007/076833
PCT Pub. Date: Jul. 12, 2007

(65) Prior Publication Data
US 2008/0269907 A1  Oct. 30, 2008

(30) Foreign Application Priority Data
Dec. 22, 2005 (DE) .......... 10 2005 062 083

(51) Int. Cl.
A61F 2/68 (2006.01)
A61F 2/58 (2006.01)
A61F 2/54 (2006.01)
B25J 17/02 (2006.01)

(52) U.S. Cl.
USPC ............ 623/61; 623/63; 623/64; 901/29

(58) Field of Classification Search
USPC ............................... 623/61, 62–65
See application file for complete search history.

(56) References Cited

U.S. PATENT DOCUMENTS

| 5,376,066 | A  | * | 12/1994 | Phillips et al. | ......... | 602/21 |
| 5,549,712 | A  |   | 8/1996  | Gammer et al. |           |        |
| 2004/0015240 | A1 | * | 1/2004 | Archer et al. | .......... | 623/62 |
| 2005/0133319 | A1 | * | 6/2005 | Wilhelm | ............... | 188/281 |
| 2007/0191959 | A1 | * | 8/2007 | Hartmann et al. | ........ | 623/17.16 |

FOREIGN PATENT DOCUMENTS

| DE | 292785 | 2/1915 |
| DE | 307338 | 6/1916 |
| DE | 307250 | 9/1917 |
| DE | 4324399 | 2/1995 |
| FR | 1112526 | 3/1956 |
| GB | 1517035 | 7/1978 |
| GB | 2109245 | 11/1982 |
| WO | 03094807 | 5/2003 |
| WO | WO 03094807 A1 * | 11/2003 |

OTHER PUBLICATIONS

International Search Report for PCT/DE2006/002310, mailed Jul. 19, 2007; 3 pgs.

* cited by examiner

Primary Examiner — David Isabella
Assistant Examiner — Jacqueline Woznicki
(74) Attorney, Agent, or Firm — Holland & Hart (57) ABSTRACT The invention relates to a hand prosthesis comprising a chassis and coupling elements for fastening the hand prosthesis to the stump of an arm and comprising at least one joint for the flexion and extension of the hand prosthesis in relation to the coupling elements, the chassis being kept in a neutral position against a spring force.

20 Claims, 7 Drawing Sheets

ARTICULATED HAND PROSTHESIS

CROSS-REFERENCE TO RELATED APPLICATIONS

This application is a national stage application, filed pursuant to 35 U.S.C. §371, of PCT application PCT/DE2006/002310 filed Dec. 21, 2006, which claims priority to DE 10 2005 062 083.3 filed Dec. 22, 2005, which is incorporated herein by reference in its entirety.

FIELD OF THE INVENTION

The invention relates to a hand prosthesis comprising a chassis and coupling elements for fastening the hand prosthesis to the stump of an arm and comprising at least one joint for the flexion and extension of the hand prosthesis in relation to the coupling elements, the chassis being kept in a neutral position against a spring force.

BACKGROUND

US 2004/0015240 A1 discloses a hand prosthesis with gripping elements on a chassis, which has a semicircular rotating element. A torsion spring is arranged between a base plate and a mounting plate and keeps the chassis with the motor-driven gripping elements in a neutral position. The chassis can be locked in different angular positions by means of a displaceable locking plate.

SUMMARY

An object of the invention is to provide a hand prosthesis to the extent that it has an appearance that is as natural as possible.

The hand prosthesis according to the invention comprises a chassis and coupling elements for fastening the hand prosthesis to the stump of an arm, and at least one joint for the flexion or extension of the hand prosthesis in relation to the coupling elements. The chassis is kept in a neutral position against a spring force provided by at least one spring element associated with the chassis, which has a progressive spring characteristic and, with increasing flexion or extension angles, offers an increasing counteracting force toward the neutral position.

To achieve an appearance of the hand prosthesis that is as natural as possible, it is intended to replicate a natural hand in its appearance, both in the way in which it functions and in the way it looks, in order to achieve improved acceptance among wearers of prostheses. In order that the impression of an artificial body part is not given when contact is made with other people or objects, it is necessary for all the parts of the prosthesis that lie at the surface to be soft in the way they are formed and for elastic parts to be included in the hand, and in particular in the region of the wrist.

In one embodiment, the joint of the hand prosthesis as such is formed as a loose joint, which is kept in a neutral or starting position by at least one spring element. This spring element is associated with the chassis and supports the latter with respect to the other parts of the joint, in particular the coupling elements or components arranged in between. The spring element is formed such that a progressive spring characteristic is obtained for increasing flexion or extension angles, so that it is possible in the neutral position of the hand to obtain a soft characteristic and easy mobility within the neutral position and in a small angular range around it. Toward the respective end positions of the hand chassis, an increased counteracting force is provided to avoid hard impact with the limits of movement. This increases the natural character of the hand prosthesis.

The spring element may be formed as a torsion spring, which operates both in the direction of extension and in the direction of flexion. Alternatively, spring elements may be respectively effective against extension or against flexion, it also being possible for a number of spring components that become effective one after the other to form a spring element having a progressive spring characteristic. It is likewise possible for the spring element to take the form of an elastomer part which, depending on the flexion angle or the extension angle, opposes turning about the flexion joint with an increased, in particular progressive, spring force. The spring element or elements may be exchangeably formed, to permit adaptation to the respective hand prosthesis or requirements of the prosthesis user.

In addition to flexion and extension movement, the chassis may be mounted rotatably about an axis substantially parallel to the longitudinal extent of the stump of the arm to allow a further rotational movement component to be provided in the wrist to make the hand prosthesis appear as natural as possible.

The joint may include a locking device, which locks the joint in a desired fixed position to allow a gripped object to be raised and held. This locking device may function both for the flexion-extension joint and for the rotary joint. The locking device may also be fitted separately in a hand prosthesis, without a corresponding spring characteristic or restoring device having to be present. The locking device may in this case have a crown gearing, which can be brought into engagement to arrest the joint. The crown gearing may be easily releasable and provide for very fine angle graduation, so that the hand prosthesis can be arrested in virtually any desired angular position.

The mechanism for the locking function can be switched on by single actuation and switched off by repeated actuation. The actuation of the locking mechanism may either be performed manually by means of a pushbutton or be performed by means of an electrically actuable drive unit.

To be able to provide a hand prosthesis with an appearance that looks as natural as possible, the flexion-extension joint according to one embodiment is arranged in the metacarpal region of the chassis. The alignment of the joint axis of the extension-flexion joint at an oblique, in particular obtuse, angle in relation to the longitudinal extent of the stump of the arm combines the properties of flexion and simultaneous abduction of the hand prosthesis. This is favorable for most day-to-day tasks.

An exemplary embodiment of the invention is explained in more detail below on the basis of the accompanying figures, in which.

Figure 1:
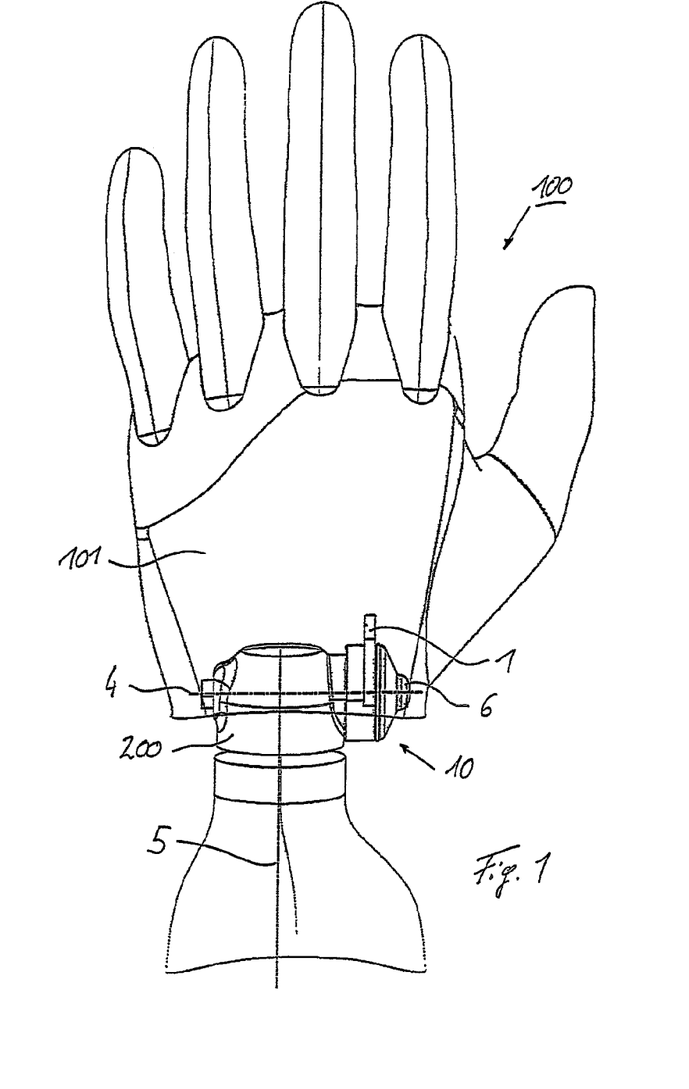
FIG. 1 shows an overall representation of a hand prosthesis in plan view.

FIG. 1 shows an overall representation of a hand prosthesis 100 in plan view, said prosthesis comprising a chassis 101, which is articulated both in the direction of flexion and in the direction of extension about a swiveling axis 4 by means of a joint device 10. The joint device 10, referred to hereafter as the joint, has a mounting plate 1 for fastening on the hand chassis 101. Furthermore, a housing 200 for coupling the hand prosthesis 100 to fastening devices on the stump of an arm is formed in the joint 10. The housing 200 may be connected to the mounting plate 1 by way of a coupling element 2 (See FIG. 3). The housing 200, and consequently the hand prosthesis 100, permit a rotational movement about an axis 5. The axis of rotation 5 is aligned substantially parallel to the longitudinal extent of the lower arm shaft. The flexion and extension swiveling axis 4 is at right angles to the axis of rotation 5.

Arranged laterally on the joint 10 is an elastic actuating element 6 for a locking device arranged within the joint 10. The actuating element 6 allows the hand chassis 101 to be locked in a chosen angular position. Likewise, the hand chassis 101 can be transferred from the locked position into an unlocked position by renewed actuation.

Figure 2:
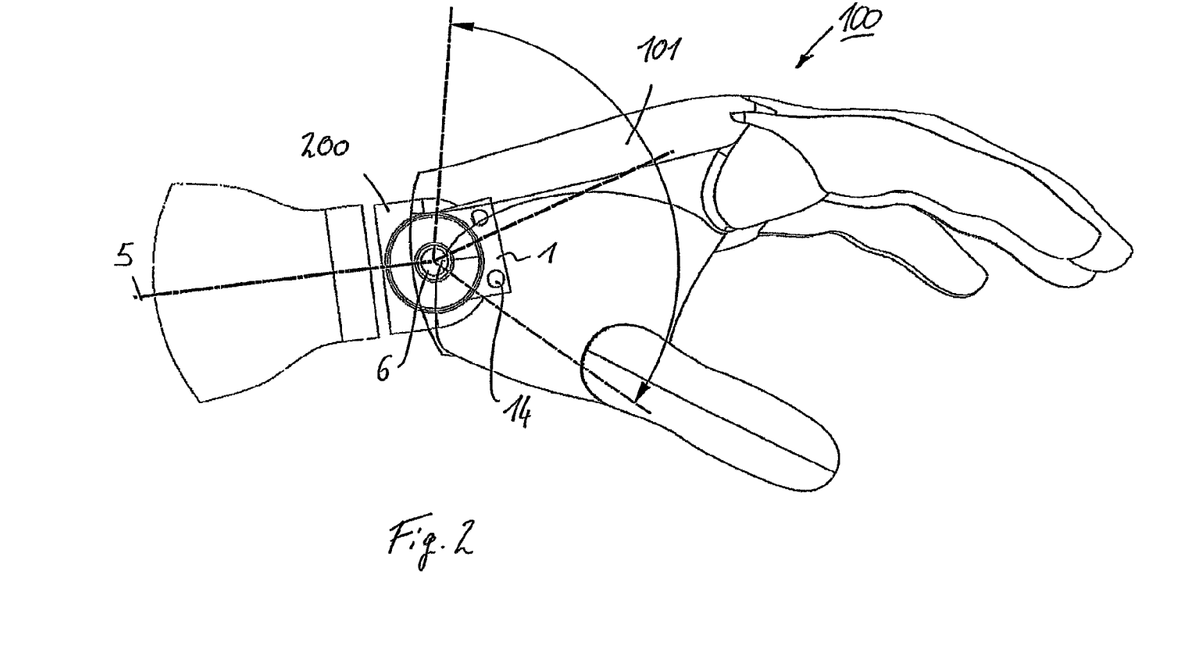
FIG. 2 shows a hand prosthesis according to FIG. 1 in side view.

FIG. 2 shows the hand prosthesis 100 in a side view, which comprises the chassis 101 and the mounting plate 1, on which the hand chassis 101 is fixed by means of bores 14 and suitable fastening means. In FIG. 2, the hand prosthesis 100 is in the neutral position and can perform a counterclockwise extending movement and a clockwise flexing movement, as indicated by the double-headed arrow. The fingers may be driven individually or together by a motor within the chassis 101 or the housing 200. The hand prosthesis 100 is urged toward the neutral position by means of a spring element 3 in the joint 10 (see FIG. 3), making it possible for the hand chassis 101 to return from an extended or flexed position into the neutral position.

Figure 3:
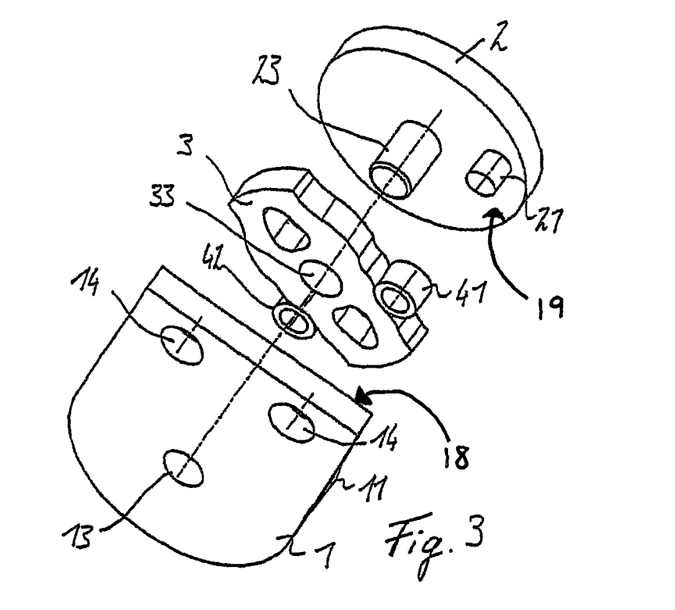
FIG. 3 shows a perspective exploded drawing of a prosthetic joint for a hand.

FIG. 3 shows several components of the joint 10, including the mounting plate 1, coupling element 2 and spring element 3. The mounting plate includes a circular frame 11, bores 14 for fastening further components of the hand prosthesis and a central bore 13 formed at the center point of the circular frame 11 for receiving a rotating pin 23 of coupling element 2. The spring element 3 in the form of an elastomer body is arranged between the coupling element 2 and the mounting plate 1 or a corresponding element of the chassis 101. The spring element 3 has a central bore 33, in which the rotating pin 23 is inserted in the fitted position. The rotating pin 23 also protrudes into the bore 13 of the mounting plate 1 in the fitted position.

Arranged or formed on the coupling element 2, which for its part may be fixed on a fastening part of the housing 200 for receiving the stump of an arm, is a pin 21, which is received by a rotating sleeve 41 on the spring element 3. Likewise formed on the mounting plate 1 is a pin 12 (which cannot be seen in FIG. 3), which is received in a rotating sleeve 42. The rotating sleeves 41, 42 rest on the opposing edge surfaces of the spring element 3 and, in one embodiment, can roll along them. The coupling element 2 and mounting plate 1 each include opposing portions 18, 19 that contact the spring element 3.

Figure 4:
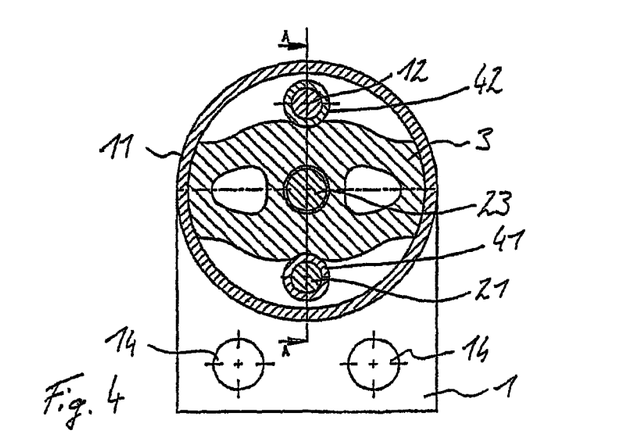
FIG. 4 shows a sectional representation of the prosthetic joint in a neutral position.

FIG. 4 shows a sectional representation of the prosthetic joint 10 for a hand in the neutral position. The two rotating sleeves 41, 42 are arranged on their respective bearing pins 21, 12 and lie opposite each other on indentations 34 (See FIG. 6) of the spring element 3. The spring element 3 has been placed in the circular frame 11, which is formed on the mounting plate 1, such that the outer circumference of the spring element 3 corresponds generally to the inner contour of the frame 11. In the present case, the spring element 3 is formed mirror-symmetrically, so that the same spring rates are obtained both in the direction of extension and in the direction of flexion. This can be varied according various embodiments, so that different spring forces are obtained for extension and flexion. Also formed in the spring element 3 are clearances 35 (see FIG. 6), which influence the spring characteristics. The larger the clearances 35 are, the softer the movement of the hand prosthesis about the neutral position.

Figure 5:
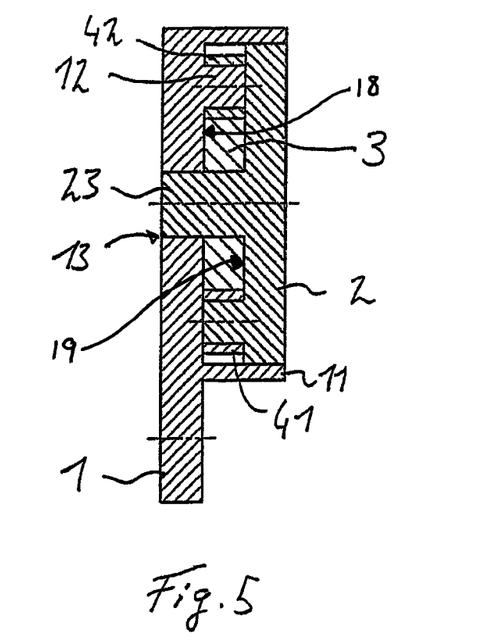
FIG. 5 shows a section along A-A of FIG. 4.

It can be seen in a sectional representation in FIG. 5 that the frame 11 is formed in one piece with the mounting plate 1, as is the bearing pin 12 for the rotating sleeve 42. The bearing pin 21 (see FIG. 3) is formed in one piece on the coupling element 2, as is the rotating pin 23.

Figure 6:
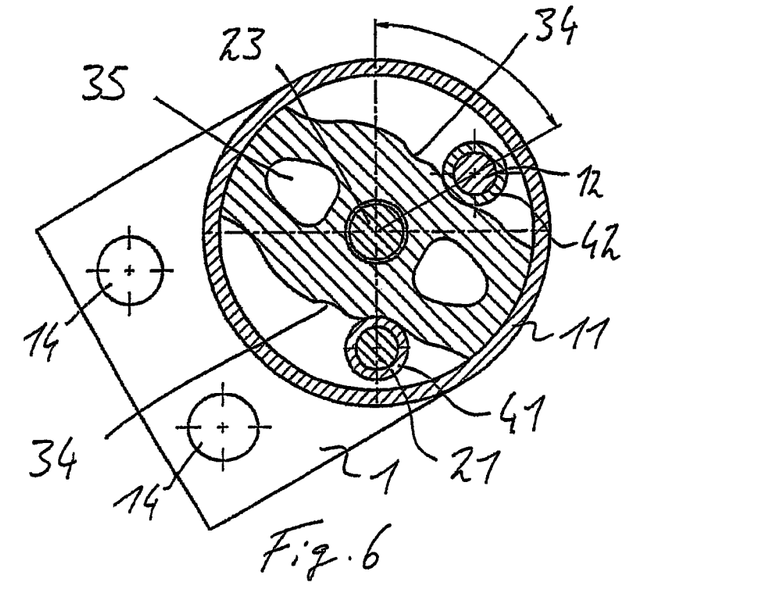
FIG. 6 shows a representation according to FIG. 4 in a position turned by 60°.

If the hand prosthesis 100 together with the mounting plate 1 is then turned in relation to the coupling element 2, as represented in FIG. 6, the bearing pins 21, 12 are displaced in relation to each other. The spring element 3, formed as a one-piece elastomer part, is compressed to achieve a progressive spring characteristic as a result of the way in which the spring element 3 is configured in the present case. This may occur for example by means of inserted components within the spring element 3 and their sequential activation in dependence on the turning angle, or by means of appropriate shaping. In the neutral position, as represented in FIG. 3, the spring element 3 has a relatively soft spring characteristic so that, when there is movement of the lower arm, the hand prosthesis 100 swings relatively loosely along with it like a natural hand. The indentations 34 have the effect of bringing about a preferential neutral position, so that the hand prosthesis 100 is always returned to this position due to the restoring forces of the spring element 3. The further the hand prosthesis 100 is turned in relation to the coupling element 2, the more the counteracting force produced by the spring element is increased, to reduce or eliminate hard impact against end stops. This corresponds to the natural sequence of movements and appearance of a hand and additionally reduces the stress on the mechanical components of the hand prosthesis 100.

Figure 9:
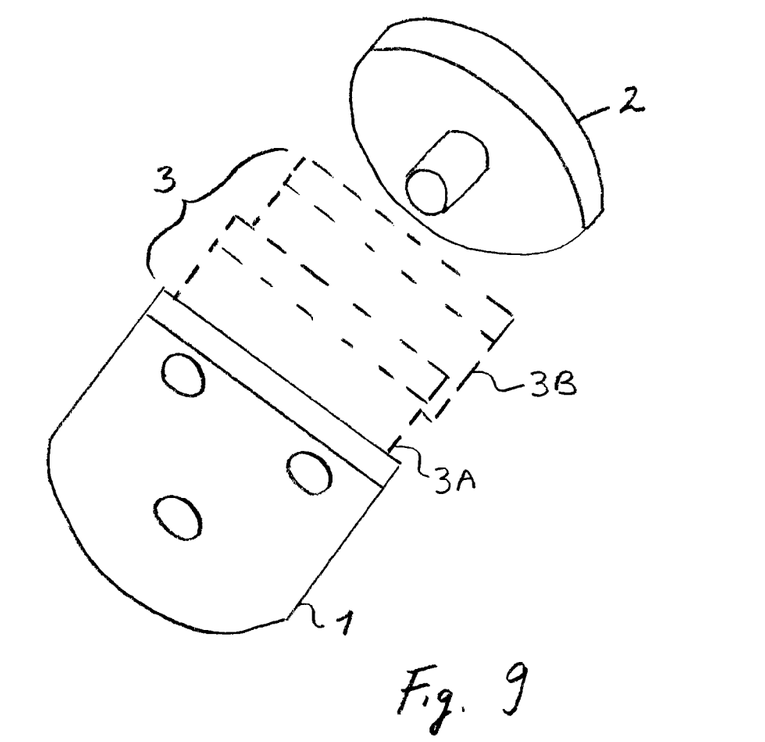
FIG. 9 shows a perspective exploded drawing of another embodiment of a prosthetic joint for a hand.

As an alternative to the one-piece configuration, the spring element 3 may also be formed by a number of separate spring elements (see schematic representation of spring elements 3A, 3B in FIG. 9). For example, different spring elements 3A 3B may be provided for extension and flexion. For example, the hand prosthesis 100 may be kept in the neutral position by the two spring elements 3A, 3B.

Figure 7:
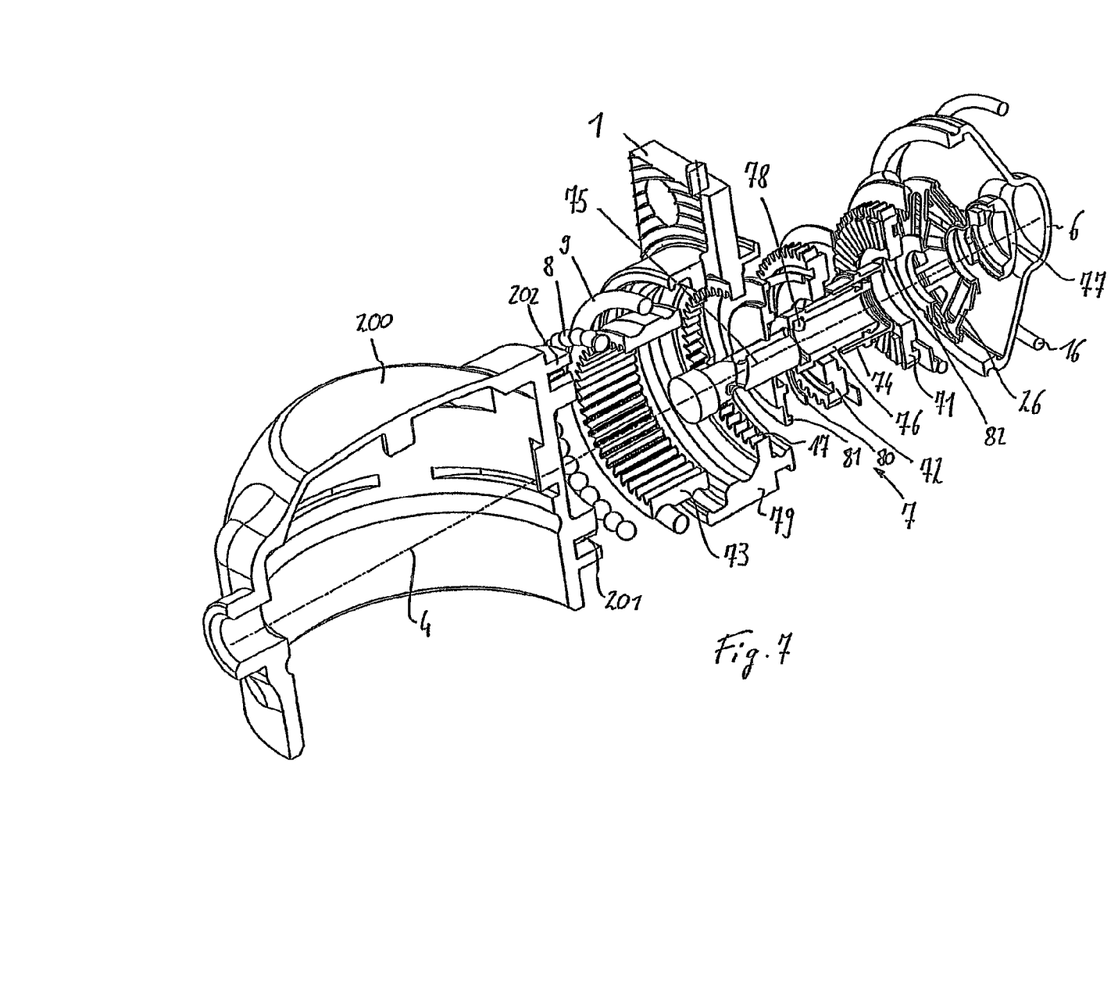
FIG. 7 shows a perspective, sectional exploded representation of a flexion lock.

FIG. 7 shows a locking device 7, which is attached to the housing 200. The mounting plate or base plate 1 for fastening the hand chassis 101 is arranged within the locking device 7. The spring element 3 described above is not shown, however due to the flat configuration of the spring element 3 easy integration with the locking device 7 or housing 200 is possible.

An external toothing 201 with a radially peripheral web 202 is formed on the housing 200. Inserted in the free space between the external toothing 201 and the web 202 is an internal toothing ring 73, which can be turned together with the chassis 101 in relation to the base plate 1. Turning is achieved by bearing balls 8, which run in corresponding ball tracks within the internal toothing ring 73 and the bearing housing 79 of the base plate 1. A sealing ring 9 serves as sealing between the housing 200 and the bearing housing 79. An internal toothing 17 is formed within the bearing housing 79, in the region of the base plate 1. A crown gearing disk 72 with external toothing and crown gearing engages in the internal toothing ring 73. In the fitted state with the joint locked, this crown gearing disk 72 engages a second, opposing crown gearing disk 71, which likewise has an external toothing and engages the internal toothing of the bearing housing 79. The crown gearing disks 71, 72 are pressed against each other and kept in engagement by means of a spring ring 80 and a cup spring 26. The cup spring 26 is supported by a pressure cap 77 with an elastic cap 6 as an actuating device. The elastic cap 6 is fixed on the base plate 1 or the bearing housing 79 in a waterproof manner by a holding ring 16. The cup spring 26 and the spring disk 80 are supported on the crown gearing disks 71, 72 by pressure disks 81, 82.

Arranged within the crown gearing disks 71, 72 is a disengaging mechanism, which when actuated moves the crown gearing disks 71, 72 apart in the axial direction. The pressure cap 77 can be displaced in the direction of the housing 200 and moves a pressure sleeve 76, in which a disengaging pin 75 and a ball 78 are guided, in the direction of the housing 200. The cup springs 26 press the pressure disk 82 in the direction of the housing 200 and exert a force on a disengaging sleeve 74 arranged around the pressure sleeve 76. The disengaging sleeve 74 has a peripheral web, which protrudes between the crown gearing disks 71, 72 and enters into positive engagement with the crown gearing disk 72 assigned to the internal toothing ring 73. The ball 78 is guided within the pressure sleeve 76 and engages the disengaging pin 75, in which a track guide in the form of the developed projection of a cardioid is provided.

If the pressure cap 77 is then moved in the direction of the housing 200, the cup spring 26 presses on the disengaging sleeve 74 via the pressure disk 82 and moves the crown gearing disk 72 axially away from the crown gearing disk 71, so that a rotation takes place about the joint axis 4. Further pressing of the pressure cap 77 makes the prestressed cup spring 26 begin to move in, the ball 78 being guided on the fixed disengaging pin 75, along the cardioid track guide in the direction of the fixed housing 200, and having the effect that the pressure sleeve 76 remains securely held on the disengaging pin 75 by way of the ball 78. The rotation about the axis 4 consequently continues to be possible.

Figure 8:
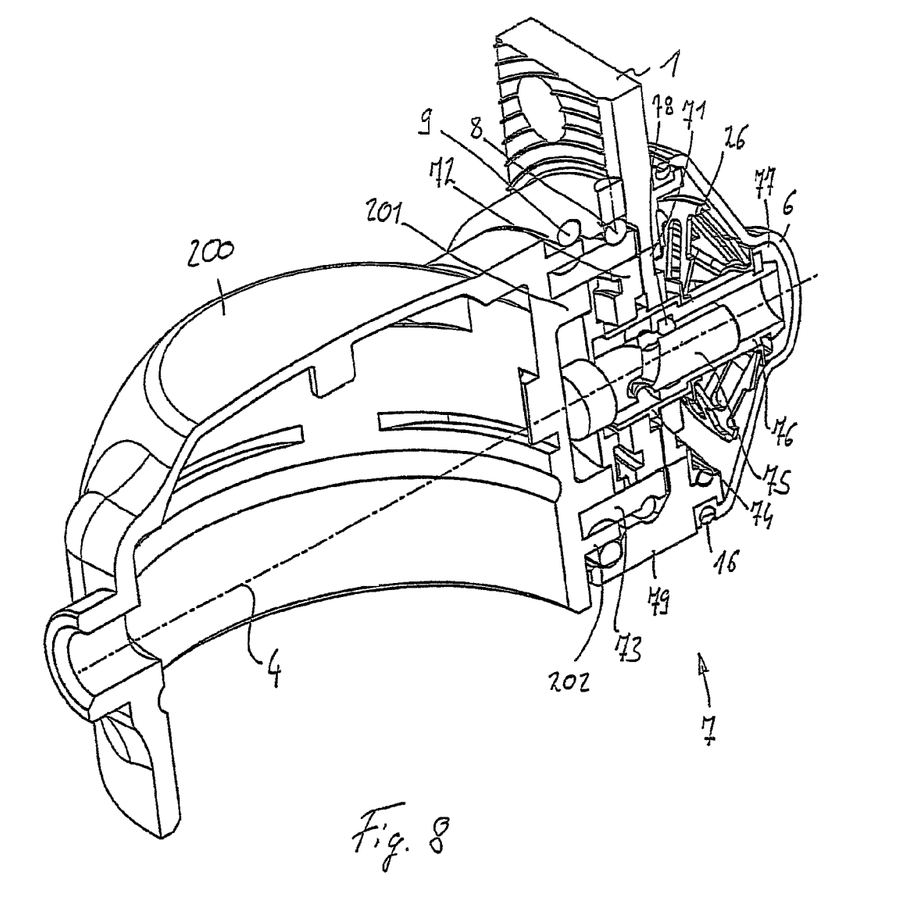
FIG. 8 shows a sectional representation of the flexion lock according to FIG. 7 in the fitted position.

By renewed actuation of the pressure cap 77, the ball 8 is moved further in the track guide of the disengaging pin 75. By moving the ball 78 out from a locking dead center position, the disengaging sleeve 74 will return to the locked position represented in FIG. 8. The mechanism works in a way analogous to a ballpoint pen or a push-push element.

The same mechanism of the locking device 7 can also be used for the locking and unlocking of the rotation about the rotational axis 5.

The invention claimed is:

1. A hand prosthesis comprising:
a chassis; and
at least one joint adapted to provide for flexion and extension movement of the chassis from a neutral position in relation to the coupling elements, the joint including first and second spring elements having progressive spring characteristics that urge the chassis from an angle of flexion or extension toward the neutral position, wherein the first and second spring elements are elastomer parts;
wherein the chassis is mounted to be rotatable about a rotation axis that is arranged at a right angle to an axis of flexion and extension movement and configured to be parallel to a longitudinal axis of a residual portion of an arm to which the hand prosthesis is mounted;
wherein the neutral position is aligned at an obtuse angle in relation to an angle that is at a right angle to the rotation axis of flexion and extension movement;
a locking device adapted to lock the joint to prevent flexion or extension movement of the chassis, the locking device being actuated in a direction along the rotation axis from a locked position that limits at least one of flexion movement and extension movement of the chassis to a released position that permits at least one of flexion movement or extension movement of the chassis.

2. A hand prosthesis comprising:
a chassis including prosthetic fingers and thumb;
a housing configured to be secured to a residual portion of an arm; and
a joint adapted to secure the chassis to the housing, the joint including a mounting plate coupled to the chassis, a coupling element coupled to the housing and the mounting plate to provide the chassis with flexion and extension movement relative to the housing, a first spring element comprising an elastomeric material and being disposed between the mounting plate and the coupling element that resiliently compresses to resist the flexion movement relative to a neutral position, and a second spring element comprising an elastomeric material and being disposed between the mounting plate and the coupling element that resiliently compresses to resist the extension movement relative to a neutral position, wherein at least one of the first and second spring elements has progressive spring characteristics;
wherein the chassis is mounted to be rotatable about an axis that is arranged at a right angle to an axis of flexion and extension movement and configured to be parallel to a longitudinal axis of the residual portion of an arm;
wherein the neutral position is aligned at an obtuse angle in relation to an angle that is at a right angle to the axis of flexion and extension movement;
a locking device adapted to lock the joint to prevent flexion or extension movement of the chassis, the locking device being actuated in a direction along the rotation axis from a locked position that limits at least one of flexion movement and extension movement of the chassis to a released position that permits at least one of flexion movement or extension movement of the chassis.

3. The hand prosthesis of claim 2 wherein the coupling element includes a rotating pin, the mounting plate includes a bore, which is capable of receiving the rotating pin to couple the coupling element to the housing.

4. The hand prosthesis of claim 3 wherein the coupling element and mounting plate each include opposing portions that contact the spring elements to resist flexion and extension movement from the neutral position.

5. The hand prosthesis of claim 2, wherein the locking device comprises a push-push element.

6. The hand prosthesis of claim 2, wherein the locking device comprises mating crown gearing disks, and operating the locking device into the released positioned included separating the crown gearing disks in a direction along the rotation axis.

7. The hand prosthesis of claim 6, wherein the locking device comprises at least one spring member that biases the crown gearing disks into contact with each other to prevent flexion or extension movement of the chassis.

8. The hand prosthesis of claim 2, wherein the locking device comprises a disengaging pin and a follower ball, the disengaging pin comprising a track and the follower ball engages the track to hold the locking device in the released position.

9. The hand prosthesis of claim 8, wherein the track is cardioid shaped.

10. A hand prosthesis comprising:

a chassis; and at least one joint adapted to secure the chassis to coupling elements on the stump of an arm to provide for flexion and extension movement of the chassis from a neutral position in relation to the coupling elements, the joint including a first spring element comprising elastomeric material that urges the chassis from an angle of flexion toward the neutral position, and a second spring element comprising elastomeric material that urges the chassis from an angle of extension toward the neutral position, wherein the first and second spring elements have progressive spring characteristics such that as the angle of flexion or extension increases during movement of the chassis, the first and second spring elements apply a correspondingly increasing force against the chassis;

wherein the chassis is mounted to be rotatable about a rotation axis that is arranged at a right angle to an axis of flexion and extension movement and configured to be parallel to a longitudinal axis of the stump of an arm;

wherein the neutral position is aligned at an obtuse angle in relation to an angle that is at a right angle to the axis of flexion and extension movement;

a locking device adapted to lock the joint to prevent flexion or extension movement of the chassis, the locking device being actuated in a direction along the rotation axis from a locked position that limits at least one of flexion movement and extension movement of the chassis to a released position that permits at least one of flexion movement or extension movement of the chassis.

11. The hand prosthesis of claim 10, wherein at least one of the spring elements is a torsion spring.

12. The hand prosthesis of claim 10 wherein the spring elements are removable from the joint to accommodate exchangeable spring elements.

13. The hand prosthesis of claim 10, wherein the locking device has crown gearing which are engaged to lock the joint.

14. The hand prosthesis of claim 10, wherein the joint is positioned such that a region of the chassis corresponding to a metacarpal region is capable of flexion or extension movement.

15. The hand prosthesis of claim 10 wherein the spring elements are configured such that the greater that an angle of flexion or extension is between the chassis and the housing, the greater force the spring elements apply to the chassis and housing to return the hand prosthesis to the neutral position.

16. The hand prosthesis of claim 10, wherein the locking device comprises a push-push element.

17. The hand prosthesis of claim 10, wherein the locking device comprises mating crown gearing disks, and operating the locking device into the released positioned included separating the crown gearing disks in a direction along the rotation axis.

18. The hand prosthesis of claim 17, wherein the locking device comprises at least one spring member that biases the crown gearing disks into contact with each other to prevent flexion or extension movement of the chassis.

19. The hand prosthesis of claim 10, wherein the locking device comprises a disengaging pin and a follower ball, the disengaging pin comprising a track and the follower ball contacts the track to hold the locking device in the released position.

20. The hand prosthesis of claim 19, wherein the track is cardioid shaped.

* * * * *